United States Patent [19]

Cantatore et al.

[11] Patent Number: 4,948,889
[45] Date of Patent: Aug. 14, 1990

[54] TRIAZINE COMPOUNDS DERIVED FROM 2,2,6,6-TETRAMETHYLPIPERIDINE

[75] Inventors: Giuseppe Cantatore, Bitonto; Franca Masina, Anzola Emilia; Valerio Borzatta, Bologna, all of Italy

[73] Assignee: Ciba-Geigy Corporation, Ardsley, N.Y.

[21] Appl. No.: 167,808

[22] Filed: Mar. 14, 1988

[30] Foreign Application Priority Data

Mar. 24, 1987 [IT] Italy ................. 19814 A/87

[51] Int. Cl.$^5$ .................. C07D 403/00; C07D 403/14
[52] U.S. Cl. ..................... 544/198; 544/212; 544/209; 544/113; 540/598; 540/575
[58] Field of Search .............. 544/212, 209, 113, 198; 540/598, 575

[56] References Cited

U.S. PATENT DOCUMENTS 4,356,287 10/1982 Loffelman et al. ................ 525/204
4,750,930 6/1988 Shapiro ............................... 544/212

FOREIGN PATENT DOCUMENTS 0107615 5/1984 European Pat. Off. ............ 544/212
0209127 1/1987 European Pat. Off. ............ 544/212

Primary Examiner—Mary C. Lee
Assistant Examiner—Robert C. Whittenbaugh
Attorney, Agent, or Firm—Harry Falber; JoAnn Villamizar

[57] ABSTRACT

A compound selected from the group consisting of compounds of the formula (I)

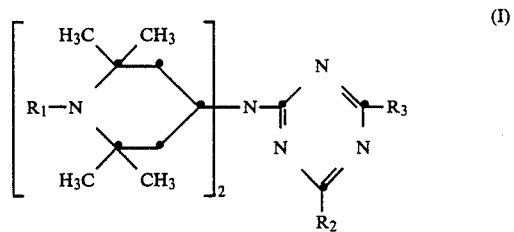

The compounds of the formula (I) are useful as light stabilizers, heat stabilizers, and oxidation stabilizers.

20 Claims, No Drawings

TRIAZINE COMPOUNDS DERIVED FROM 2,2,6,6-TETRAMETHYLPIPERIDINE

The present invention relates to novel triazine compounds, the use thereof and to the organic material stabilized with the aid of said compounds against thermal, oxidative or light-induced degradation.

It is known that synthetic polymers undergo progressive changes in their physical properties, such as loss of mechanical strength and colour changes, when they are exposed to sunlight or other sources of ultraviolet light.

To retard the deleterious effect of ultraviolet radiation on synthetic polymers, it has been proposed to use various additives having light-stabilizing properties, such as certain derivatives of benzophenone and benzotriazole, nickel complexes, substituted benzoic acid esters, alkylidenemalonates, cyanoacrylates, aromatic oxamides and sterically hindered amines.

EP-A No. 107 615 describes 2,4-bis[2,2,6,6-tetramethyl-4-piperidylamino]-1,3,5-triazines and their light-stabilizing activity for polyolefin.

EP-A No. 209 127 and EP-B No. 1-82 244 disclose 2-[N,N-bis(2,2,6,6-tetramethyl-4-piperidyl)amino]-1,3,5-triazines and the use thereof as stabilizers for synthetic polymers.

The present invention relates to compounds selected from the group consisting of compounds of the formulae (I), (Ia) and (Ib)

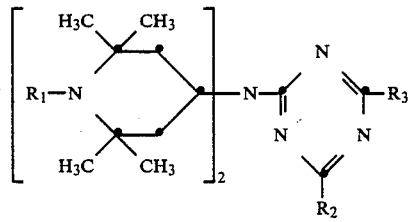
(I)

in which $R_1$ is hydrogen, O·, —NO, —CH$_2$CN, $C_1$-$C_8$alkyl, allyl, benzyl, OH-monosubstituted $C_2$-$C_4$alkyl or $C_1$-$C_8$acyl, $R_2$ and $R_3$ are independently of one another

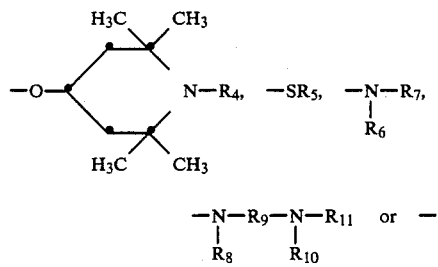

and $R_2$ is additionally a group of the formula (II)

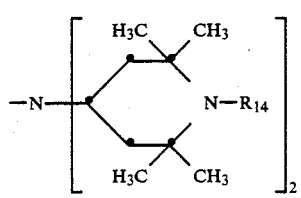
(II)

$R_4$ and $R_{14}$ have one of the meanings given for $R_1$, $R_5$ is $C_1$-$C_{18}$alkyl, $C_5$-$C_{12}$cycloalkyl unsubstituted or substituted by $C_1$-$C_4$alkyl, phenyl unsubstituted or substituted by $C_1$-$C_4$alkyl, $C_7$-$C_{12}$phenylalkyl unsubstituted or substituted at the phenyl ring by $C_1$-$C_4$alkyl or is $C_2$-$C_4$alkyl substituted in the 2, 3 or 4 position by OH, by $C_1$-$C_{12}$alkoxy or by di($C_1$-$C_4$alkyl)amino, $R_6$ is hydrogen, $C_1$-$C_{18}$alkyl, $C_5$-$C_{12}$cycloalkyl unsubstituted or substituted by $C_1$-$C_4$alkyl, $C_7$-$C_{12}$phenylalkyl unsubstituted or substituted at the phenyl ring by $C_1$-$C_4$alkyl, $C_2$-$C_4$alkyl substituted in the 2, 3 or 4 position by —OH or by $C_1$-$C_{12}$alkoxy, tetrahydrofurfuryl or a group of the formula (III)

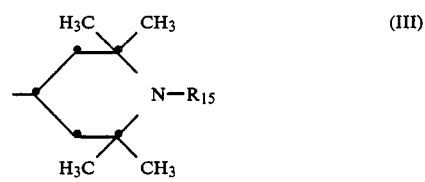
(III)

where $R_{15}$ has one of the meanings given for $R_1$, $R_7$ is $C_7$-$C_{12}$-phenylalkyl unsubstituted or substituted at the phenyl ring by $C_1$-$C_4$alkyl or is tetrahydrofurfuryl or when $R_6$ is a group of the formula (III), $R_7$ is additionally $C_2$-$C_4$alkyl substituted in the 2, 3 or 4 position by —OH or by $C_1$-$C_{12}$alkoxy, or $R_6$ and $R_7$, together with the nitrogen atom to which they are linked, form part of a 7-membered heterocyclic ring containing one or two nitrogen atoms, $R_8$ is hydrogen, $C_1$-$C_{18}$alkyl, $C_5$-$C_{12}$cycloalkyl unsubstituted or substituted by $C_1$-$C_4$alkyl, $C_7$-$C_{12}$phenylalkyl unsubstituted or substituted at the phenyl ring by $C_1$-$C_4$alkyl, $C_2$-$C_4$alkyl substituted in the 2, 3 or 4 position by —OH, by $C_1$-$C_{12}$alkoxy or by di($C_1$-$C_4$alkyl)amino, tetrahydrofurfuryl or a group of the formula (III), $R_9$ is $C_2$-$C_{10}$alkylene, $R_{10}$ and $R_{11}$ are independently of one another $C_1$-$C_{18}$alkyl or $R_{10}$ and $R_{11}$, together with the nitrogen to which they are linked, form part of a 5-membered to 7-membered heterocyclic ring, $R_{12}$ is $C_2$-$C_4$alkylene, $R_{13}$ is hydrogen, $C_1$-$C_{18}$alkyl, phenyl unsubstituted or substituted by $C_1$-$C_{12}$alkyl or a group of the formula (III) and n is an integer from 2 to 20;

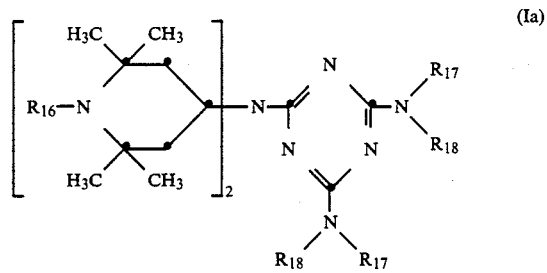
(Ia)

wherein $R_{16}$ is hydrogen, methyl or benzyl, the radicals $R_{17}$ are independently of one another $C_1$-$C_{18}$alkyl and the radicals $R_{18}$ are independently of one another hydrogen or a group of the formula (IV)

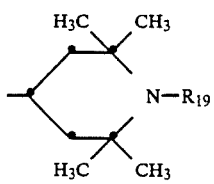

where $R_{19}$ has one of the meanings given for $R_{16}$;

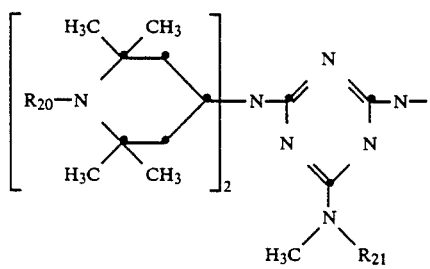

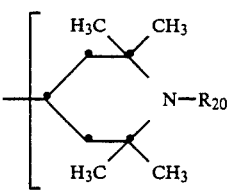

wherein the radicals $R_{20}$ are independently of one another hydrogen, methyl or benzyl and $R_{21}$ is $C_8$–$C_{18}$alkyl or $C_3$–$C_{18}$alkoxyalkyl.

$R_1$, $R_4$, $R_{14}$ and $R_{15}$ as $C_1$–$C_8$alkyl are for example methyl, ethyl, propyl, butyl, pentyl, hexyl, heptyl or octyl. $C_1$–$C_4$alkyl, in particular methyl, is preferred.

$R_1$, $R_4$, $R_5$, $R_6$, $R_7$, $R_8$, $R_{14}$ and $R_{15}$ as $C_2$–$C_4$alkyl which is mono-substituted by —OH, preferably in the 2 or 3 position, are for example 2-hydroxyethyl, 2-hydroxypropyl, 3-hydroxypropyl, 2-hydroxybutyl or 4-hydroxybutyl. 2-Hydroxyethyl is preferred.

$R_1$, $R_4$, $R_{14}$ and $R_{15}$ as $C_1$–$C_8$acyl may be benzoyl or an aliphatic $C_1$–$C_8$acyl group, e.g. $C_1$–$C_8$alkanoyl or $C_3$–$C_8$alkenoyl. Examples of an aliphatic acyl group are formyl, acetyl, propionyl, butyryl, valeryl, caproyl, acryloyl and crotonoyl. Acetyl is preferred.

$R_5$, $R_6$, $R_8$, $R_{10}$, $R_{11}$, $R_{13}$ and $R_{17}$ as $C_1$–$C_{18}$alkyl are for example methyl, ethyl, propyl, isopropyl, butyl, 2-butyl, isobutyl, t-butyl, pentyl, hexyl, heptyl, octyl, 2-ethylhexyl, 1,1,3,3-tetramethylbutyl, nonyl, decyl, undecyl, dodecyl, tridecyl, tetradecyl, hexadecyl or octadecyl. $R_5$, $R_6$ and $R_8$ are preferably $C_1$–$C_{12}$alkyl, and $R_{10}$, $R_{11}$ and $R_{13}$ are preferably $C_1$–$C_4$alkyl, whereas $R_{17}$ as $C_1$–$C_8$alkyl is preferred.

$R_5$, $R_6$ and $R_8$ as $C_5$–$C_{12}$cycloalkyl which may optionally be substituted by $C_1$–$C_4$alkyl, in particular methyl, are for example cyclopentyl, cyclohexyl, methylcyclohexyl, dimethylcyclohexyl, trimethylcyclohexyl, t-butylcyclohexyl, cyclooctyl or cyclododecyl. $C_5$–$C_8$cycloalkyl, in particular cyclohexyl, unsubstituted or substituted by methyl is preferred.

$R_5$ as phenyl substituted by $C_1$–$C_4$alkyl is for example methylphenyl, dimethylphenyl, trimethylphenyl, t-butylphenyl or 2,6-di-t-butyl-4-methylphenyl.

$R_{13}$ as phenyl substituted by $C_1$–$C_{12}$alkyl is for example methylphenyl, dimethylphenyl, trimethylphenyl, t-butylphenyl, 2,6-di-t-butyl-4-methylphenyl, 4-(1,1,3,3-tetramethylbutyl)phenyl or nonylphenyl.

$R_5$, $R_6$, $R_7$ and $R_8$ as $C_7$–$C_{12}$phenylalkyl which may optionally be substituted at the phenyl ring by $C_1$–$C_4$alkyl are for example benzyl, methylbenzyl, dimethylbenzyl, trimethylbenzyl, t-butylbenzyl or 2-phenylethyl. Benzyl is preferred.

$R_5$, $R_6$, $R_7$ and $R_8$ as $C_2$–$C_4$alkyl substituted by $C_1$–$C_{12}$alkoxy, preferably $C_1$–$C_4$alkoxy, are for example 2-methoxyethyl, 2-ethoxyethyl, 2-butoxyethyl, 3-methoxypropyl, 3-ethoxypropyl, 3-butoxypropyl, 3-octyloxypropyl, 3-(2-ethylhexyloxy)propyl, 3-dodecyloxypropyl or 4-methoxybutyl.

$R_5$ and $R_8$ as $C_2$–$C_4$alkyl substituted by di($C_1$–$C_4$alkyl)amino are for example 2-dimethylaminoethyl, 2-diethylaminoethyl, 2-dibutylaminoethyl, 3-dimethylaminopropyl, 3-diethylaminopropyl or 3-dibutylaminopropyl.

If $R_6$ and $R_7$, together with the nitrogen atom to which they are linked, form part of a 7-membered heterocyclic ring containing one or two nitrogen atoms, said ring is e.g. 1-hexahydroazepinyl, 1-homopiperazinyl, 5,5,7-trimethyl-1-homopiperazinyl or 4,5,5,7-tetramethyl-1-homopiperazinyl.

$R_9$ as $C_2$–$C_{10}$alkylene is for example ethylene, propylene, tetramethylene, pentamethylene, 2,2-dimethyl-1,3-propylene, hexamethylene, octamethylene or decamethylene. $C_2$–$C_6$alkylene is preferred.

If $R_{10}$ and $R_{11}$, together with the nitrogen to which they are attached, form a 5-membered to 7-membered heterocyclic group, said group is e.g. 1-pyrrolidyl, 1-piperidyl, 4-morpholinyl, 4-thiomorpholinyl, 1-piperazinyl, 4-methyl-1-piperazinyl, 1-hexahydroazepinyl, 1-homopiperazinyl, 5,5,7-trimethyl-1-homopiperazinyl or 4,5,5,7-tetramethyl-1-homopiperazinyl. Except the nitrogen, to which the radicals $R_{10}$ and $R_{11}$ are linked, the heterocyclic group may optionally contain another heteroatom such as O, S or N.

$R_{12}$ as $C_2$–$C_4$alkylene is for example ethylene, propylene, tetramethylene. Ethylene is preferred.

$R_{13}$ as a group of the formula (III) is preferably 2,2,6,6-tetramethyl-4-piperidyl or 1,2,2,6,6-pentamethyl-4-piperidyl.

$R_{21}$ as $C_3$–$C_{18}$alkoxyalkyl is preferably $C_2$–$C_4$alkyl substituted in the 2, 3 or 4 position by $C_1$–$C_{12}$alkoxy, in particular $C_1$–$C_4$alkoxy. Examples are 2-methoxyethyl, 2-ethoxyethyl, 2-butoxyethyl, 3-methoxypropyl, 3-ethoxypropyl, 3-butoxypropyl, 3-octyloxypropyl, 3-(2-ethylhexyloxy)propyl, 3-dodecyloxypropyl and 4-methoxybutyl.

$R_{21}$ as $C_8$–$C_{18}$alkyl is for example octyl, 2-ethylhexyl, 1,1,3,3-tetramethylbutyl, nonyl, decyl, undecyl, dodecyl, tridecyl, tetradecyl, hexadecyl or octadecyl. $C_8$–$C_{12}$alkyl is preferred.

Those compounds of the formula (I) are preferred, wherein $R_2$ and $R_3$ are as defined above and $R_5$ is $C_1$–$C_{18}$ alkyl, phenyl, cyclohexyl unsubstituted or substituted by $C_1$–$C_4$alkyl, $R_6$ is hydrogen, $C_1$–$C_{18}$-alkyl, $C_5$–$C_8$cycloalkyl unsubstituted or substituted by $C_1$–$C_4$alkyl, benzyl, $C_2$–$C_4$alkyl substituted in the 2, 3 or 4 position by —OH or by $C_1$–$C_{12}$alkoxy, tetrahydrofurfuryl or a group of the formula (III), $R_7$ is benzyl unsubstituted or substituted at the phenyl ring by $C_1$–$C_4$alkyl, tetrahydrofurfuryl or when $R_6$ is a group of the formula (III), $R_7$ is additionally $C_2$–$C_4$alkyl substituted in the 2, 3 or 4 position by —OH or by $C_1$–$C_{12}$alkoxy, or the radicals $R_6$ and $R_7$, together with the nitrogen atom to which they are linked, form part of a 7-membered heterocyclic ring containing one or two nitrogen atoms, $R_8$ is hydrogen, $C_1$-$C_{18}$alkyl, $C_5$-$C_8$cycloalkyl unsubstituted or substituted by $C_1$-$C_4$alkyl, benzyl, $C_2$-$C_4$alkyl substituted in the 2, 3 or 4 position by —OH, by $C_1$-$C_{12}$alkoxy or by di($C_1$-$C_4$alkyl)amino, tetrahydrofurfuryl or a group of the formula (III).

Those compounds of the formula (I) are especially preferred, wherein $R_2$ and $R_3$ are as defined above and $R_5$ is $C_1$-$C_{18}$alkyl or phenyl, $R_6$ is hydrogen, $C_1$-$C_{18}$alkyl, cyclohexyl unsubstituted or substituted by $C_1$-$C_4$alkyl, benzyl, $C_2$-$C_3$alkyl substituted in the 2 or 3 position by —OH or by $C_1$-$C_{12}$alkoxy, tetrahydrofurfuryl or a group of the formula (III), $R_7$ is benzyl, tetrahydrofurfuryl or when $R_6$ is a group of the formula (III), $R_7$ is additionally $C_2$-$C_3$alkyl substituted in the 2 or 3 position by —OH or by $C_1$-$C_8$alkoxy, or the radicals $R_6$ and $R_7$, together with the nitrogen atom to which they are linked, form part of a 7-membered heterocyclic ring containing one or two nitrogen atoms, $R_8$ is hydrogen, $C_1$-$C_{18}$alkyl, cyclohexyl unsubstituted or substituted by $C_1$-$C_4$alkyl, benzyl, $C_2$-$C_3$alkyl substituted in the 2 or 3 position by —OH, by $C_1$-$C_{12}$alkoxy or by di($C_1$-$C_4$alkyl)amino, tetrahydrofurfuryl or a group of the formula (III), $R_9$ is $C_2$-$C_6$alkylene, $R_{10}$ and $R_{11}$ are independently of one another $C_1$-$C_{12}$alkyl, or $R_{10}$ and $R_{11}$, together with the nitrogen atom to which they are linked, form 1-pyrrolidyl, 1-piperidyl, 4-morpholinyl or 1-hexahydroazepinyl, $R_{12}$ is $C_2$-$C_4$alkylene, $R_{13}$ is hydrogen or $C_1$-$C_{12}$alkyl and n is an integer from 2 to 20.

The radicals $R_1$, $R_4$, $R_{14}$ and $R_{15}$ are preferably hydrogen, —$CH_2CN$, $C_1$-$C_4$alkyl, allyl, benzyl, acetyl or $C_2$-$C_3$alkyl substituted in the 2 or 3 position by —OH, and are in particular hydrogen or methyl.

Compounds of the formula (I) which are of interest are those, wherein $R_1$ is hydrogen or methyl, $R_2$ and $R_3$ are as defined above, $R_4$ and $R_{14}$ are hydrogen or methyl, $R_5$ is $C_1$-$C_{12}$alkyl, $R_6$ and $R_8$ are independently of one another hydrogen, $C_1$-$C_{12}$alkyl, cyclohexyl, benzyl or a group of the formula (III) wherein $R_{15}$ is hydrogen or methyl, $R_7$ is benzyl, tetrahydrofurfuryl or when $R_6$ is a group of the formula (III), $R_7$ is additionally 3-($C_1$-$C_4$alkoxy)propyl, or $R_6$ and $R_7$, together with the nitrogen atom to which they are linked, form 1-hexahydroazepinyl, 5,5,7-trimethyl-1,4-diazepan-1-yl or 4,5,5,7-tetramethyl-1,4-diazepan-1-yl, $R_9$ is $C_2$-$C_6$alkylene, $R_{10}$ and $R_{11}$ are $C_1$-$C_4$alkyl, $R_{12}$ is $C_2$-$C_4$alkylene, $R_{13}$ is hydrogen or $C_1$-$C_{12}$alkyl and n is an integer from 2 to 15.

Compounds of the formula (I) which are also of interest are those, wherein $R_1$ is hydrogen or methyl, $R_2$ and $R_3$ are independently of one another

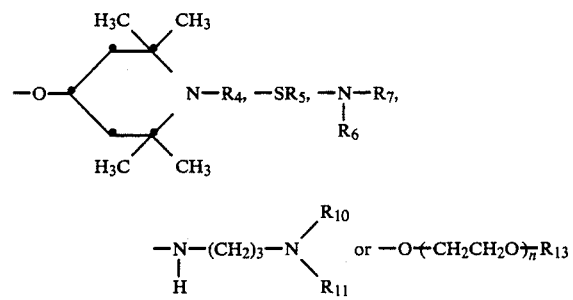

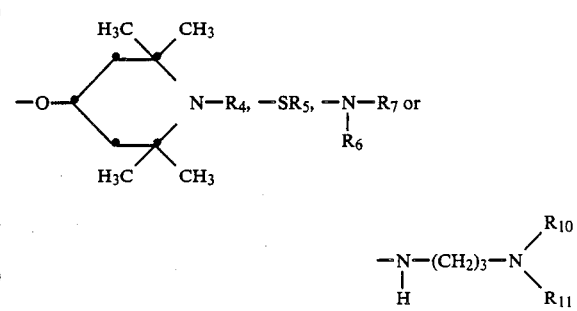

and $R_2$ is additionally a group of the formula (II), $R_4$ and $R_{14}$ are hydrogen or methyl, $R_5$ is $C_4$-$C_{12}$alkyl, $R_6$ is hydrogen, 2,2,6,6-tetramethyl-4-piperidyl or 1,2,2,6,6-pentamethyl-4-piperidyl, $R_7$ is benzyl, tetrahydrofurfuryl, or when $R_6$ is 2,2,6,6-tetramethyl-4-piperidyl or 1,2,2,6,6-pentamethyl-4-piperidyl, $R_7$ is additionally 3-methoxypropyl or 3-ethoxypropyl, $R_{10}$ and $R_{11}$ are independently of one another $C_1$-$C_4$alkyl, $R_{13}$ is $C_1$-$C_{12}$alkyl and n is an integer from 2 to 10.

Compounds of the formula (I) which are of particular interest are those, wherein $R_1$ is hydrogen or methyl, $R_2$ and $R_3$ are independently of one another

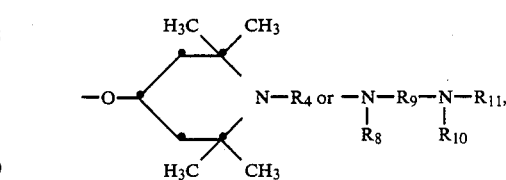

and $R_2$ is additionally a group of the formula (II), $R_4$ and $R_{14}$ are hydrogen or methyl, $R_5$ is $C_8$-$C_{12}$alkyl, $R_6$ is hydrogen, 2,2,6,6-tetramethyl-4-piperidyl or 1,2,2,6,6-pentamethyl-4-piperidyl, $R_7$ is tetrahydrofurfuryl, or when $R_6$ is 2,2,6,6-tetramethyl-4-piperidyl or 1,2,2,6,6-pentamethyl-4-piperidyl, $R_7$ is additionally 3-methoxypropyl or 3-ethoxypropyl and $R_{10}$ and $R_{11}$ are independently of one another methyl or ethyl.

Compounds of the formula (I) wherein $R_2$ and $R_3$ are —$SR_5$ or —O$(-R_{12}O)_nR_{13}$, in particular a group

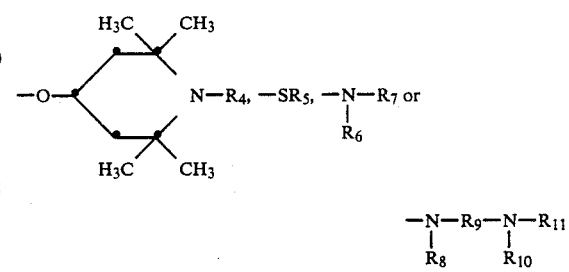

and $R_2$ is additionally a group of the formula (II) are also preferred.

Those compounds of the formula (I) are especially preferred, wherein $R_1$ is hydrogen or methyl, $R_2$ and $R_3$ are independently of one another and $R_2$ is additionally a group of the formula (II) where $R_{14}$ is hydrogen or methyl, $R_4$ is hydrogen or methyl, $R_5$ is $C_1$-$C_{12}$alkyl, $R_6$ and $R_8$ are independently of one another hydrogen or a group of the formula (III) where $R_{15}$ is hydrogen or methyl, $R_7$ is tetrahydrofurfuryl or when $R_6$ is a group of the formula (III), $R_7$ is additionally 3-($C_1$-$C_4$alkoxy)propyl, or $R_6$ and $R_7$, together with the nitrogen atom to which they are linked, form 5,5,7-trimethyl-1,4-diazepan-1-yl, $R_9$ is $C_2$-$C_6$alkylene and $R_{10}$ and $R_{11}$ are independently of one another $C_1$-$C_4$alkyl.

Preferred examples of compounds of the formula (I) are:

(a) 2-[N,N-bis(2,2,6,6-tetramethyl-4-piperidyl)amino]-4,6-bis[tetrahydrofurfurylamino]-1,3,5-triazine, (b) 2-[N,N-bis(2,2,6,6-tetramethyl-4-piperidyl)amino]-4,6-bis[5,5,7-trimethyl-1,4-diazepan-1-yl]-1,3,5-triazine, (c) 2-[N,N-bis(2,2,6,6-tetramethyl-4-piperidyl)amino]-4,6-bis[N-(2,2,6,6-tetramethyl-4-piperidyl)-tetrahydrofurfurylamino]-1,3,5-triazine, (d) 2-[N,N-bis(2,2,6,6-tetramethyl-4-piperidyl)amino]-4,6-bis[1,2,2,6,6-pentamethyl-4-piperidyloxy]-1,3,5-triazine, (e) 2,4-bis[N,N-bis(2,2,6,6-tetramethyl-4-piperidyl)amino]-6-[3-(diethylamino)propylamino]-1,3,5-triazine, (f) 2-[N,N-bis(1,2,2,6,6-pentamethyl-4-piperidyl)amino]-4,6-bis[1,2,2,6,6-pentamethyl-4-piperidyloxy]-1,3,5-triazine, (g) 2,4-bis[N,N-bis(1,2,2,6,6-pentamethyl-4-piperidyl)amino]-6-[3-(diethylamino)propylamino]-1,3,5-triazine, (h) 2-[N,N-bis(2,2,6,6-tetramethyl-4-piperidyl)amino]-4,6-bis[n-dodecylthio]-1,3,5-triazine, (i) 2,4-bis[N,N-bis(2,2,6,6-tetramethyl-4-piperidyl)amino]-6-[n-dodecylthio]-1,3,5-triazine, (j) 2-[N,N-bis(2,2,6,6-tetramethyl-4-piperidyl)amino]-4,6-bis[N-(2,2,6,6-tetramethyl-4-piperidyl)-3-methoxypropylamino]-1,3,5-triazine.

The compounds (c), (d), (e), (f), (i) and (j) are especially preferred.

Compounds of the formula (Ia) wherein $R_{16}$ is benzyl are preferred.

Those compounds of the formula (Ia) are especially preferred, wherein $R_{16}$ is hydrogen or methyl, the radicals $R_{17}$ are identical and are $C_1$-$C_8$alkyl and the radicals $R_{18}$ are identical and are 1,2,2,6,6-pentamethyl-4-piperidyl or 2,2,6,6-tetramethyl-4-piperidyl.

A preferred example of compounds of the formula (Ia) is: 2-[N,N-bis(1,2,2,6,6-pentamethyl-4-piperidyl)amino]-4,6-bis[N-(1,2,2,6,6-pentamethyl-4-piperidyl)-n-butylamino]-1,3,5-triazine.

Those compounds of the formula (Ib) are preferred, wherein the radical $R_{20}$ are independently of one another hydrogen or methyl and $R_{21}$ is $C_8$-$C_{12}$alkyl.

Compounds of the formula (Ib) wherein the radicals $R_{20}$ are benzyl are also preferred.

Preferred examples of compounds of the formula (Ib) are:

2,4-bis[N,N-bis(1,2,2,6,6-pentamethyl-4-piperidyl)amino]-6-[N-(methyl)-n-octylamino]-1,3,5-triazine, 2,4-bis[N,N-bis(1,2,2,6,6-pentamethyl-4-piperidyl)amino]-6-[N-(methyl)-n-dodecylamino]-1,3,5-triazine.

The compounds of the formula (I) can be prepared by processes known per se, e.g. by reacting cyanuric chloride, in any order, with the compounds of the formulae (V), (VI) and (VII)

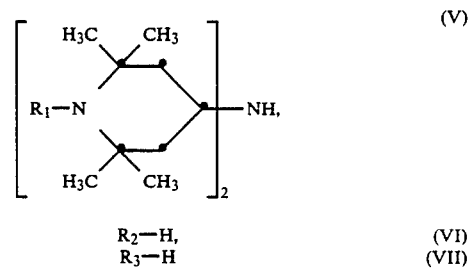

$$R_2-H, \quad (VI)$$
$$R_3-H \quad (VII)$$

in which $R_1$, $R_2$ and $R_3$ are as defined above.

The ratio of the reagents is preferably theoretical, particularly in the substitution of the first and second chlorine of the cyanuric chloride, but an excess of up to 20% of reagent is also possible in the substitution of the third chlorine.

The reactions are conveniently carried out in inert solvents, for example acetone, methyl ethyl ketone, methyl isobutyl ketone, dioxane, tetrahydrofuran, dibutyl ether, benzene, toluene, xylene, trimethylbenzene, ethylbenzene, decalin, octane, decane, chlorobenzene or N-methylpyrrolidone, in the presence of an organic or inorganic base, preferably sodium or potassium hydroxide or carbonate, in quantities at least equivalent to the hydrochloric acid released in the reaction.

The substitution of the first chlorine of the cyanuric chloride takes preferably place at temperatures between $-30°$ and $40°$ C., in particular between $-10°$ and $30°$ C., the substitution of the second chlorine takes preferably place between $40°$ and $150°$ C., in particular between $50°$ and $140°$ C., and the substitution of the third chlorine takes preferably place between $100°$ and $200°$ C., in particular between $140°$ and $180°$ C.

The various reaction stages can be carried out in a single reactor and in the same reaction medium without isolating the intermediates, or after separating and, if desired, purifying the latter.

The compounds of the formulae (Ia) and (Ib) can be prepared by analogy to the compounds of the formula (I).

The starting materials are known and can be prepared by known methods, if not commercial available.

As mentioned at the outset the compounds of the formula (I), (Ia) or (Ib) are very effective in improving the light stability, heat stability or oxidation stability of organic materials, in particular synthetic polymers. Especially, the outstanding oxidation stabilizing efficiency of the instant compounds is surprising.

Therefore, a further object of the invention is a composition comprising an organic material subject to thermal, oxidative or light-induced degradation and at least one compound of the formula (I), (Ia) or (Ib).

Those compositions are preferred, wherein the organic material is a synthetic polymer, in particular a polyolefin, e.g. polyethylene or polypropylene.

Examples of organic materials which can be stabilized by compounds of the formula (I), (Ia) or (Ib) are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefines and diolefines with each other or with other vinyl monomers, such as, for example, ethylene/propylene, linear low density polyethylene (LLDPE) and its mixtures with low density polyethylene (LDPE), propylene/butene-1, ethylene/hexene ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene; as well as mixtures of such copolymers and their mixtures with polymers mentioned in 1) above, for example polypropylene/ethylene-propylene-copolymers, LDPE/EVA, LDPE/EAA, LLDPE/EVA and LLDPE/EAA.

3a. Hydrocarbon resins (for example $C_5$–$C_9$) and hydrogenated modifications thereof (for example tackyfiers).

4. Polystyrene, poly-(p-methylstyrene), poly-(α-methylstyrene).

5. Copolymers of styrene or α-methylstyrene with dienes or acrylic derivatives, such as, for example, styrene/butadiene, styrene/acrylonitrile, styrene/alkyl methacrylate, styrene/maleic anhydride, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadien, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine; as well as their copolymers with olefins mentioned in (1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylenediamine and adipic acid; polyamides prepared from hexamethylene diamine and isophthalic or/and terephthalic acid and optionally an elastomer as modifier, for example poly-2,4,4,-trimethylhexamethylene terephthalamide or poly-m-phenylene isophthalamide. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2,-(4-hydroxyphenyl)-propane] terephthalate and polyhydroxybenzoates as well as block-copolyether-esters derived from polyethers having hydroxyl end groups.

18. Polycarbonates and polyester-carbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or the cellulose ethers, such as methylcellulose; rosins and their derivatives.

27. Mixtures of polymers as mentioned above, for example PP/EPDM, Polyamide 6/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/butadiene copolymers.

The compounds of the formula (I), (Ia) or (Ib) can be used in mixtures with the material to be stabilized in various proportions depending on the nature of the polymer, the end use and the presence of other additives. In general, it is advantageous to use 0.01 to 5% by weight of the compounds of the formula (I), (Ia) or (Ib), relative to the weight of the polymers, preferably between 0.05 and 1%. The compounds of the formula (I), (Ia) or (Ib) can be incorporated into the polymeric materials by various processes, such as dry blending in the form of powders, or wet blending in the form of solutions or suspensions or in the form of a masterbatch; in these operations, the polymer can be employed in the form of powder, granules, solutions, suspensions or in the form of a latex.

The material stabilized with the compounds of the formula (I), (Ia) or (Ib) can be used for the preparation of moulded articles, films, tapes, monofilaments, surface-coatings and the like.

If desired, other conventional additives for synthetic polymers, such as antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (I), (Ia) or (Ib) with the material to be stabilized.

Examples of additives which can be mixed with the compounds of the formula (I), (Ia) or (Ib) are in particular:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha$,$\alpha$-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl] terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl)isocyanurate.

1.6. Acylaminophenols, for example 4-hydroxyanilide of lauric acid, 4-hydroxyanilide of stearic acid, 2,4-bis(octylmercapto)-6-(3,5-di-tert-butyl-4-hydroxyanilino)-s-triazine, octyl N-(3,5-di-tert-butyl-4-hydroxyphenyl)carbamate.

1.7. Esters of $\beta$-(3,5-di-tert-butyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.9. Esters of β-(3,5-dicyclohexyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.10. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-trimethylene-diamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example, 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoneoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane tetracarboxylate, 1,1'-(1,2-ethanediyl)bis(3,3,5,5-tetramethylpiperazinone).

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-disubstituted oxanilides and mixtures of o- and p-ethoxy-disubstituted oxanilides.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic acid dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4'-biphenylene diphosphonite, 3,9-bis(2,4-di-tert-butylphenoxy)-2,4,8,10-tetraoxa-3,9-diphosphaspiro[5.5]undecane.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example copper salts in combination with iodides and/or phosphorus compounds and salts of divalent manganese.

7. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flame-proofing agents, antistatic agents and blowing agents.

EXAMPLE 1

(A) Preparation of 2-[N,N-bis(2,2,6,6-tetramethyl-4-piperidyl)amino]-4,6-dichloro-1,3,5-triazine 29.5 g (0.1 mol) of bis(2,2,6,6-tetramethyl-4-piperidyl)amine are slowly added to a solution, cooled to −10° C., of 18.45 g (0.1 mol) of cyanuric chloride in 160 ml of xylene, maintaining the temperature at about 0° C. After the end of the addition, the mixture is stirred for 3 hours at room temperature, 4.4 g (0.11 mol) of powdered sodium hydroxide are added and stirring is continued for a further 2 hours at room temperature.

The mixture is filtered, and the residue is washed with $H_2O$ and dried at 110° C. in vacuo (2 mbar).

The product obtained has a melting point of 251°-252° C.

Analysis for $C_{21}H_{36}Cl_2N_6$: Calculated: Cl 15.99%. Found: Cl 16.01%.

(B) Preparation of 2-[N,N-bis(2,2,6,6-tetramethyl-4-piperidyl)amino]-4,6-bis[N-(2,2,6,6-tetramethyl-4-piperidyl)-octylamino]-1,3,5-triazine 44.3 g (0.1 mol) of 2-[N,N-bis(2,2,6,6-tetramethyl-4-piperidyl)amino]-4,6-dichloro-1,3,5-triazine, 56.38 g (0.21 mol) of 2,2,6,6-tetramethyl-4-octylaminopiperidine and 250 ml of xylene are heated under reflux for 4 hours.

8.8 g (0.22 mol) of powdered sodium hydroxide are added and the mixture is heated for a further 16 hours under reflux, the water of reaction being separated off.

The mixture is filtered at 60°–70° C., and the solution obtained is evaporated in vacuo (24 mbar).

The residue is crystallized from acetone.

The product obtained has a melting point of 117°–118° C.

Analysis for $C_{55}H_{106}N_{10}$: Calculated: C 72.79%; H 11.77%; N 15.43%. Found: C 72.64%; H 11.80%; N 15.44%.

The same compound can be obtained by means of a procedure in a single reactor, by reacting 1 mol of cyanuric chloride in xylene first with 1 mol of bis(2,2,6,6-tetramethyl-4-piperidyl)amine and then with 2 mol of 2,2,6,6-tetramethyl-4-octylaminopiperidine without isolation of the dichlorotriazine formed as an intermediate.

EXAMPLES 2–9

Following the procedure described in Example 1 and using the appropriate reagents, the following compounds of the formula

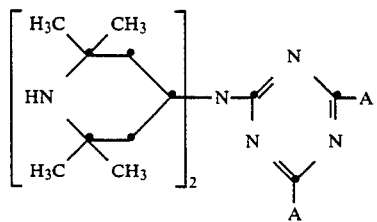

are prepared.

| Example | A | Melting point (°C.) |
|---|---|---|
| 2 | $H_3C-\underset{\underset{CH_3}{\vert}}{\overset{\overset{CH_3}{\vert}}{C}}-CH_2-\underset{\underset{CH_3}{\vert}}{\overset{\overset{CH_3}{\vert}}{C}}-NH-$ | 207–208 |
| 3 | (oxolan-2-ylmethyl)NH– (CH₂NH– attached to tetrahydrofuran ring) | 204–205 |
| 4 | 2,2,6,6-tetramethylpiperazinyl group (HN, H₃C, H₃C, CH₃, CH₃, N–) | 245–246 |
| 5 | 2,2,6,6-tetramethyl-1-methyl-4-piperidyl (HN-piperidyl with N–CH₃) | 340–341 |
| 6 | 2,2,6,6-tetramethyl-1-ethyl-4-piperidyl (N–C₂H₅) | 319–320 |
| 7 | 2,2,6,6-tetramethyl-1-n-butyl-4-piperidyl (N–C₄H₉-n) | 247–248 |
| 8 | 2,2,6,6-tetramethyl-1-(3-methoxypropyl)-4-piperidyl (N–(CH₂)₃OCH₃) | 242–244 |
| 9 | 2,2,6,6-tetramethyl-1-(oxiranylmethyl)-4-piperidyl (N–CH₂-oxirane) | 252–253 |

EXAMPLE 10

Preparation of 2-[N,N-bis(2,2,6,6-tetramethyl-4-piperidyl)amino]-4,6-bis[1,2,2,6,6-pentamethyl-4-piperidyloxy]-1,3,5-triazine 34.2 g (0.2 mol) of 1,2,2,6,6-pentamethyl-4-hydroxypiperidine and 1 g of anhydrous potassium carbonate are added to a solution of 44.3 g (0.1 mol) of 2-[N,N-bis(2,2,6,6-tetramethyl-4-piperidyl)amino]-4,6-dichloro-1,3,5-triazine in 250 ml of xylene.

Subsequently, 56.1 g (1.0 mol) of potassium hydroxide are slowly added under stirring, not exceeding the temperature of 40° C. After the addition of 6.8 g (0.02 mol) of tetrabutylammonium hydrogen sulfate the mixture is heated at 90° C. for 2 hours under stirring. Then, the mixture is cooled and filtered. The organic solvent is evaporated in vacuo (24 mbar) and the residue is washed with water and crystallized from acetone.

After filtration and drying, the product of melting point 199°–200° C. is obtained.

Analysis for $C_{41}H_{76}N_8O_2$: Calculated: C 69.06%; H 10.74%; N 15.71%. Found: C 68.88%; H 10.69%; N 15.65%.

EXAMPLE 11

Preparation of 2-[N,N-bis(2,2,6,6-tetramethyl-4-piperidyl)amino]-4,6-bis[n-dodecylthio]-1,3,5-triazine Under stirring 2.53 g (0.11 mol) of sodium are slowly added to a solution of 20.3 g (0.11 mol) of 1-dodecanthiol in 130 ml of xylene, heated at 110° C.

After the addition, the mixture is heated at 120° C. for 2 hours. 22.1 g (0.05 mol) of 2-[N,N-bis(2,2,6,6-tetramethyl-4-piperidyl)amino]-4,6-dichloro-1,3,5-triazine are then added, heating the mixture for 8 hours under reflux.

The mixture is cooled, the organic solution is separated off by filtration and the solvent is evaporated in vacuo (24 mbar). The residue is washed with water and crystallized from acetone.

After filtration and drying, the product of melting point 62°-63° C. is obtained.

Analysis for $C_{45}H_{86}N_6S_2$: Calculated: C 69.71%; H 11.18%; N 10.84%. Found: C 69.77%; H 11.17%; N 10.80%.

EXAMPLE 12

(A) Preparation of 2,4-bis[N,N-bis(2,2,6,6-tetramethyl-4-piperidyl)amino]-6-chloro-1,3,5-triazine 59.1 g (0.2 mol) of bis(2,2,6,6-tetramethyl-4-piperidyl)amine are added to a solution of 18.45 g (0.1 mol) of cyanuric chloride in 300 ml of xylene at 20°-25° C., maintaining this temperature.

After the end of the addition, the mixture is stirred for ½ hour at 20°-25° C. and heated for 3 hours at 130° C.

138.2 g (1 mol) of comminuted anhydrous potassium carbonate are added, and the mixture is heated under reflux for 3 hours and then for a further 16 hours with the water of reaction being separated off.

The mixture thus obtained is evaporated in vacuo (24 mbar) and the residue is washed repeatedly with water, until a negative reaction for Cl$^-$ is obtained, and treated with warm acetone.

After filtration and drying, a product of melting point 321°-322° C. is obtained.

Analysis for $C_{39}H_{72}ClN_9$: Calculated: Cl 5.05%. Found: Cl 5.02%.

(B) Preparation of 2,4-bis[N,N-bis(2,2,6,6-tetramethyl-4-piperidyl)amino]-6-[3-(diethylamino)propylamino]-1,3,5-triazine 63.2 g (0.09 mol) of 2,4-bis[N,N-bis(2,2,6,6-tetramethyl-4-piperidyl)amino]-6-chloro-1,3,5-triazine, 13.02 g (0.1 mol) of 3-(diethylamino)propylamine and 250 ml of xylene are heated under reflux for 2 hours.

4.4 g (0.11 mol) of powdered sodium hydroxide are added and the mixture is heated for a further 16 hours under reflux, the water of reaction being separated off. The mixture is filtered at 80° C. and the solution is evaporated in vacuo till half volume.

From the xylenic solution a product is crystallized by cooling to room temperature.

The product is separated off by filtration and, after drying, has a melting point of 222°-224° C.

Analysis for $C_{46}H_{89}N_{11}$: Calculated: C 69.39%; H 11.27%; N 19.35%. Found: C 69.06%; H 11.20%; N 19.24%.

EXAMPLE 13

Preparation of 2,4-bis[N,N-bis(2,2,6,6-tetramethyl-4-piperidyl)amino]-6-[n-dodecylthio]-1,3,5-triazine Following the procedure described in Example 11 and using 20.3 g (0.11 mol) of 1-dodecanthiol, 2.53 g (0.11 mol) of sodium and 70.25 g (0.1 mol) of 2,4-bis[N,N-bis(2,2,6,6-tetramethyl-4-piperidyl)amino]-6-chloro-1,3,5-triazine in 250 ml of xylene, the product of melting point 168°-170° C. is obtained.

Analysis for $C_{51}H_{97}N_9S$: Calculated: C 70.53%; H 11.26%; N 14.52%. Found: C 69.98%; H 11.22%; N 14.39%.

EXAMPLE 14

Preparation of 2-[N,N-bis(1,2,2,6,6-pentamethyl-4-piperidyl)amino]-4,6-bis[N-(1,2,2,6,6-pentamethyl-4-piperidyl)-ethylamino]-1,3,5-triazine 36.96 g (0.05 mol) of the compound from Example 6 are dissolved in a solution of 18.4 g (0.4 mol) of formic acid in 120 ml of water, 12 g (0.4 mol) of paraformaldehyde are added and the mixture is heated under reflux for 12 hours. After cooling to room temperature, the reaction mixture is treated with a solution of 20 g (0.5 mol) of sodium hydroxide in 100 ml of water. The resulting precipitate is separated off by filtration, washed with copious amounts of water and dried at 120° C. in vacuo (2 mbar).

The product obtained has a melting point of 328°-329° C.

Analysis for $C_{47}H_{90}N_{10}$: Calculated: C 70.98%; H 11.41%; N 17.61%. Found: C 70.40%; H 11.40%; N 17.48%.

EXAMPLES 15-18

Following the procedure described in Example 14 and using the appropriate reagents, the following compounds of the formula

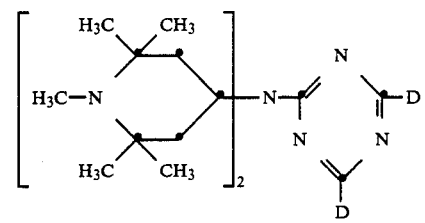

are prepared.

| Example | D | Melting point (°C.) |
|---------|---|---------------------|
| 15 | ![structure with H3C, CH3, H3C—N, N—C4H9-n] | 149-151 |

| Example | D | Melting point (°C.) |
|---|---|---|
| 16 | H₃C  CH₃ / H₃C—N / H₃C  CH₃ ring with N—C₈H₁₇-n | 100–102 |
| 17 | H₃C  CH₃ / H₃C—N / H₃C  CH₃ ring with N—(CH₂)₃OCH₃ | 258–260 |
| 18 | H₃C  CH₃ / H₃C—N / H₃C  CH₃ ring with —O— | 223–225 |

EXAMPLES 19–23

Following the procedure described in Example 14 but using the appropriate reagents, the following compounds of the formula

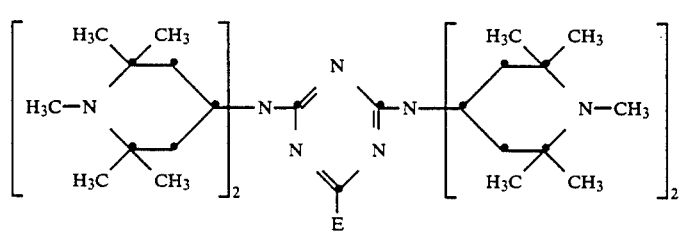

are prepared.

| Example | E | Melting point (°C.) |
|---|---|---|
| 19 | n-H₁₇C₈—N— / CH₃ | 128–130 |
| 20 | H₃C(CH₂)₃CHCH₂—N— / C₂H₅   CH₃ | 230–231 |
| 21 | n-H₂₅C₁₂—N— / CH₃ | 154–156 |
| 22 | H₉C₄O(CH₂)₃—N— / CH₃ | 213–215 |
| 23 | H₅C₂\ N—(CH₂)₃—N— / H₅C₂       H | 229–232 |

The stabilizing efficiency of the compounds of formula (I), (Ia) or (Ib) is illustrated by the examples which follow, wherein some compounds obtained in the preparation examples are used as antioxidants and as light stabilizers for polypropylene.

EXAMPLE 24

1 g of each of the compounds indicated in Table 1 and 1 g of calcium stearate are mixed in a slow mixer with 1000 g of polypropylene powder of melt index=2 g/10 minutes (measured at 230° C. and 2.16 kg).

The mixtures are extruded twice at 200°–220° C. to give polymer granules which are then converted into plates of 1 mm thickness (mould according to DIN 53451) by compression-moulding for 3 minutes at 220° C.

The plates thus obtained are exposed in an oven with forced air circulation, maintained at a temperature of 135° C., until embrittlement occurs.

The results are shown in Table 1.

TABLE 1

| Stabilizer | Time to embrittlement (hours) |
|---|---|
| Without stabilizer | 250 |
| Compound of Example 1 | 1370 |
| Compound of Example 7 | 1280 |
| Compound of Example 8 | 1280 |
| Compound of Example 9 | 1510 |
| Compound of Example 12 | 1510 |
| Compound of Example 14 | 1540 |
| Compound of Example 15 | 1540 |
| Compound of Example 16 | 1440 |
| Compound of Example 17 | 1250 |
| Compound of Example 20 | 1390 |
| Compound of Example 21 | 1320 |
| Compound of Example 23 | 1510 |

EXAMPLE 25

1 g of each of the compounds indicated in Table 2, 0.5 g of tris(2,4-di-t-butylphenyl)phosphite, 0.5 g of pentaerythritol tetrakis[3-(3,5-di-t-butyl-4-hydroxyphenyl)-propionate] and 1 g of calcium stearate are mixed in a slow mixer with 1000 g of polypropylene powder of melt index=3 g/10 minutes (measured at 230° C. and 2.16 kg).

The mixtures are extruded at 200°–220° C. to give polymer granules which are then converted into stretched tapes of 50 μm thickness and 2.5 mm width, using a pilot type apparatus (Leonard-Sumirago (VA) Italy) under the following conditions:

extruder temperature: 210°–230° C.
head temperature: 240°–260° C.
stretch ratio: 1:6

The tapes thus prepared are exposed, mounted on a white card, in a model 65 WR Weather-O-Meter (ASTM G 26-77), with a black panel temperature of 63° C.

The residual tenacity is measured on samples, taken after various times of exposure to light, by means of a constant-speed tensometer; the exposure time in hours needed to halve the initial tenacity ($T_{50}$) is then calculated.

The results are shown in Table 2.

TABLE 2

| Stabilizer | $T_{50}$ (hours) |
|---|---|
| Without stabilizer | 400 |
| Compound of Example 4 | 1890 |
| Compound of Example 7 | 2300 |
| Compound of Example 9 | 2000 |
| Compound of Example 10 | >2100 |
| Compound of Example 14 | 2100 |

We claim:

1. A compound of the formulae (I)

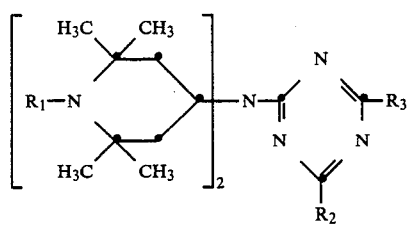

in which $R_1$ is hydrogen, O, —NO, —CH$_2$CN, $C_1$–$C_8$alkyl, allyl, benzyl, OH-monosubstituted $C_2$–$C_4$alkyl or $C_1$–$C_8$alkanoyl, $C_3$–$C_8$alkenyl or benzoyl, $R_2$ and $R_3$ are are independently of one another

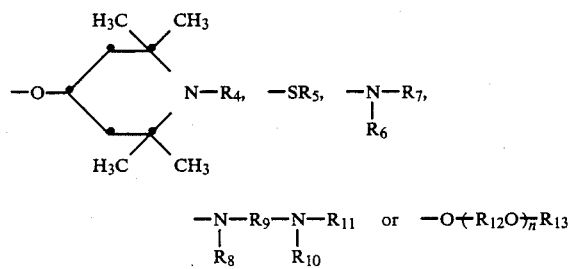

and $R_2$ is additionally a group of the formula (II)

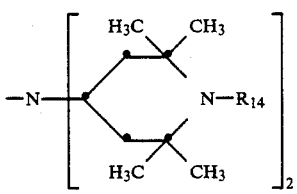

$R_4$ and $R_{14}$ have one of the meanings given for $R_1$, $R_5$ is $C_1$–$C_{18}$alkyl, $C_5$–$C_{12}$cycloalkyl unsubstituted or substituted by $C_1$–$C_4$alkyl, phenyl unsubstituted or substituted by $C_1$–$C_4$alkyl, $C_7$–$C_{12}$phenylalkyl unsubstituted or substituted at the phenyl ring by $C_1$–$C_4$alkyl or is $C_2$–$C_4$alkyl substituted in the 2, 3 or 4 position by OH, by $C_1$–$C_{12}$alkoxy or by di($C_1$–$C_4$alkyl)amino, $R_6$ is hydrogen, $C_1$–$C_{18}$alkyl, $C_5$–$C_{12}$cycloalkyl unsubstituted or substituted by $C_1$–$C_4$alkyl, $C_7$–$C_{12}$phenylalkyl unsubstituted or substituted at the phenyl ring by $C_1$–$C_4$alkyl, $C_2$–$C_4$alkyl substituted in the 2, 3 or 4 position by —OH or by $C_1$–$C_{12}$alkoxy, tetrahydrofurfuryl or a group of the formula (III)

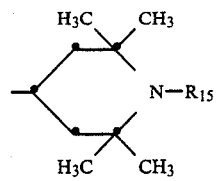

where $R_{15}$ has one of the meanings given for $R_1$, $R_7$ is $C_7$–$C_{12}$-phenylalkyl unsubstituted or substituted at the phenyl ring by $C_1$–$C_4$alkyl or is tetrahydrofurfuryl or when $R_6$ is a group of the formula (III), $R_7$ is additionally $C_2$–$C_4$alkyl substituted in the 2, 3 or 4 position by —OH or by $C_1$–$C_{12}$alkoxy, or $R_6$ and $R_7$, together with the nitrogen atom to which they are linked, form part of a 7-membered heterocyclic ring containing one or two nitrogen atoms, $R_8$ is hydrogen, $C_1$–$C_{18}$alkyl, $C_5$–$C_{12}$cycloalkyl unsubstituted or substituted by $C_1$–$C_4$alkyl, $C_7$–$C_{12}$phenylalkyl unsubstituted or substituted at the phenyl ring by $C_1$–$C_4$alkyl, $C_2$–$C_4$alkyl substituted in the 2, 3 or 4 position by —OH, by $C_1$–$C_{12}$alkoxy or by di($C_1$–$C_4$alkyl)amino, tetrahydrofurfuryl or a group of the formula (III), $R_9$ is $C_2$–$C_{10}$alkylene, $R_{10}$ and $R_{11}$ are independently of one another $C_1$–$C_{18}$alkyl or $R_{10}$ and $R_{11}$, together with the nitrogen to which they are linked, form part of a 5-membered to 7-membered heterocyclic ring, $R_{12}$ is $C_2$–$C_4$alkylene, $R_{13}$ is hydrogen, $C_1$–$C_{18}$alkyl, phenyl unsubstituted or substituted by $C_1$–$C_{12}$alkyl or a group of the formula (III) and n is an integer from 2 to 20.

2. A compound of the formula (I) according to claim 1, wherein $R_5$ is $C_1$–$C_{18}$alkyl, phenyl, cyclohexyl unsubstituted or substituted by $C_1$–$C_4$alkyl, $R_6$ is hydrogen, $C_1$–$C_{18}$alkyl, $C_5$–$C_8$cycloalkyl unsubstituted or substituted by $C_1$–$C_4$alkyl, benzyl, $C_2$–$C_4$alkyl substituted in the 2, 3 or 4 position by —OH or by $C_1$–$C_{12}$alkoxy, tetrahydrofurfuryl or a group of the formula (III), $R_7$ is benzyl unsubstituted or substituted at the phenyl ring by $C_1$–$C_4$alkyl, tetrahydrofurfuryl or when $R_6$ is a group of the formula (III), $R_7$ is additionally $C_2$–$C_4$alkyl substituted in the 2, 3 or 4 position by —OH or by $C_1$–$C_{12}$alkoxy, or the radicals $R_6$ and $R_7$, together with the nitrogen atom to which they are linked, form part of a 7-membered heterocyclic ring containing one or two nitrogen atoms, $R_8$ is hydrogen, $C_1$–$C_{18}$alkyl, $C_5$–$C_8$cycloalkyl unsubstituted or substituted by $C_1$–$C_4$alkyl, benzyl, $C_2$–$C_4$alkyl substituted in the 2, 3 or 4 position by —OH, by $C_1$–$C_{12}$alkoxy or by di($C_1$–$C_4$alkyl)amino, tetrahydrofurfuryl or a group of the formula (III).

3. A compound of the formula (I) according to claim 1, wherein $R_5$ is $C_1$–$C_{18}$alkyl or phenyl, $R_6$ is hydrogen, $C_1$–$C_{18}$alkyl, cyclohexyl unsubstituted or substituted by $C_1$–$C_4$alkyl, benzyl, $C_2$–$C_3$alkyl substituted in the 2 or 3 position by —OH or by $C_1$–$C_{12}$alkoxy, tetrahydrofurfuryl or a group of the formula (III), $R_7$ is benzyl, tetrahydrofurfuryl or when $R_6$ is a group of the formula (III), $R_7$ is additionally $C_2$–$C_3$alkyl substituted in the 2 or 3 position by —OH or by $C_1$–$C_8$alkoxy, or the radicals $R_6$ and $R_7$, together with the nitrogen atom to which they are linked, form part of a 7-membered heterocyclic ring containing one or two nitrogen atoms, $R_8$ is hydrogen, $C_1$–$C_{18}$alkyl, cyclohexyl unsubstituted or substituted by $C_1$–$C_4$alkyl, benzyl, $C_2$–$C_3$alkyl substituted in the 2 or 3 position by —OH, by $C_1$–$C_{12}$alkoxy or by di($C_1$–$C_4$alkyl)amino, tetrahydrofurfuryl or a group of the formula (III), $R_9$ is $C_2$–$C_6$alkylene, $R_{10}$ and $R_{11}$ are independently of one another $C_1$–$C_{12}$alkyl, or $R_{10}$ and $R_{11}$, together with the nitrogen atom to which they are linked, form 1-pyrrolidyl, 1-piperidyl, 4-morpholinyl or 1-hexahydroazepinyl, $R_{12}$ is $C_2-C_4$alkylene, $R_{13}$ is hydrogen or $C_1-C_{12}$alkyl and n is an integer from 2 to 20.

4. A compound of the formula (I) according to claim 1, wherein $R_1$, $R_4$, $R_{14}$ and $R_{15}$ are independently of one another hydrogen, —CH$_2$CN, $C_1-C_4$alkyl, allyl, benzyl, acetyl or $C_2-C_3$alkyl substituted in the 2 or 3 position by —OH.

5. A compound of the formula (I) according to claim 1, wherein $R_1$, $R_4$, $R_{14}$ and $R_{15}$ are independently of one another hydrogen or methyl.

6. A compound of the formula (I) according to claim 1, wherein $R_1$ is hydrogen or methyl, $R_4$ and $R_{14}$ are hydrogen or methyl, $R_5$ is $C_1-C_{12}$alkyl, $R_6$ and $R_8$ are independently of one another hydrogen, $C_1-C_{12}$alkyl, cyclohexyl, benzyl or a group of the formula (III) wherein $R_{15}$ is hydrogen or methyl, $R_7$ is benzyl, tetrahydrofurfuryl or when $R_6$ is a group of the formula (III), $R_7$ is additionally 3-($C_1-C_4$alkoxy)propyl, or $R_6$ and $R_7$, together with the nitrogen atom to which they are linked, form 1-hexahydroazepinyl, 5,5,7-trimethyl-1,4-diazepan-1-yl or 4,5,5,7-tetramethyl-1,4-diazepan-1-yl, $R_9$ is $C_2-C_6$alkylene, $R_{10}$ and $R_{11}$ are $C_1-C_4$alkyl, $R_{12}$ is $C_2-C_4$alkylene, $R_{13}$ is hydrogen or $C_1-C_{12}$alkyl and n is an integer from 2 to 15.

7. A compound of the formula (I) according to claim 1, wherein $R_1$ is hydrogen or methyl, $R_2$ and $R_3$ are independently of one another

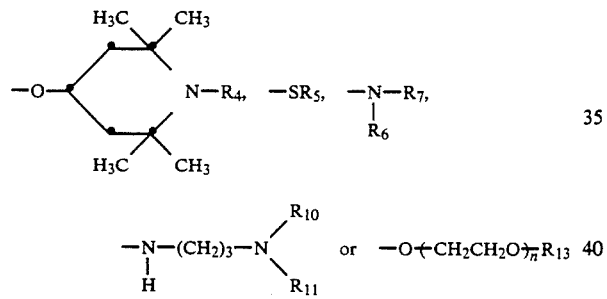

and $R_2$ is additionally a group of the formula (II), $R_4$ and $R_{14}$ are hydrogen or methyl, $R_5$ is $C_4-C_{12}$alkyl, $R_6$ is hydrogen, 2,2,6,6-tetramethyl-4-piperidyl or 1,2,2,6,6-pentamethyl-4-piperidyl, $R_7$ is benzyl, tetrahydrofurfuryl, or when $R_6$ is 2,2,6,6-tetramethyl-4-piperidyl or 1,2,2,6,6-pentamethyl-4-piperidyl, $R_7$ is additionally 3-methoxypropyl or 3-ethoxypropyl, $R_{10}$ and $R_{11}$ are independently of one another $C_1-C_4$alkyl, $R_{13}$ is $C_1-C_{12}$alkyl and n is an integer from 2 to 10.

8. A compound of the formula (I) according to claim 1, wherein $R_1$ is hydrogen or methyl, $R_2$ and $R_3$ are independently of one another

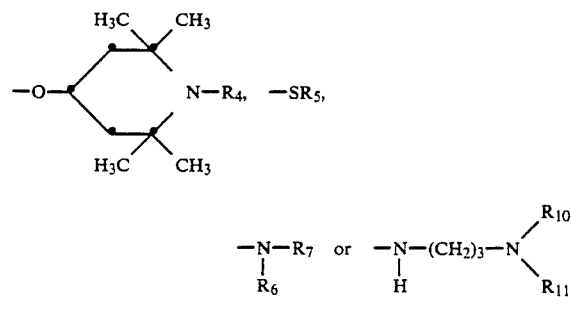

and $R_2$ is additionally a group of the formula (II), $R_4$ and $R_{14}$ are hydrogen or methyl, $R_5$ is $C_8-C_{12}$alkyl, $R_6$ is hydrogen, 2,2,6,6-tetramethyl-4-piperidyl or 1,2,2,6,6-pentamethyl-4-piperidyl, $R_7$ is tetrahydrofurfuryl, or when $R_6$ is 2,2,6,6-tetramethyl-4-piperidyl or 1,2,2,6,6-pentamethyl-4-piperidyl, $R_7$ is additionally 3-methoxypropyl or 3-ethoxypropyl and $R_{10}$ and $R_{11}$ are independently of one another methyl or ethyl.

9. A compound of the formula (I) according to claim 1, wherein $R_2$ and $R_3$ are independently of one another a group —SR$_5$ and $R_2$ is additionally a group of the formula (II).

10. A compound of the formula (I) according to claim 1, wherein $R_2$ and $R_3$ are independently of one another a group —O$(\!-\!R_{12}O)_n R_{13}$ and $R_2$ is additionally a group of the formula (II).

11. A compound of the formula (I) according to claim 1, wherein $R_2$ and $R_3$ are independently of one another

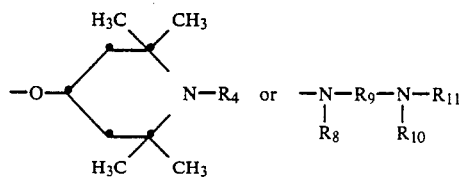

and $R_2$ is additionally a group of the formula (II).

12. A compound of the formula (I) according to claim 1, wherein $R_1$ is hydrogen or methyl, $R_2$ and $R_3$ are independently of one another

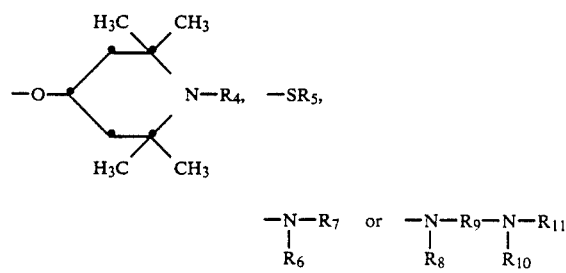

and $R_2$ is additionally a group of the formula (II) where $R_{14}$ is hydrogen or methyl, $R_4$ is hydrogen or methyl, $R_5$ is $C_1-C_{12}$alkyl, $R_6$ and $R_8$ are independently of one another hydrogen or a group of the formula (III) where $R_{15}$ is hydrogen or methyl, $R_7$ is tetrahydrofurfuryl or when $R_6$ is a group of the formula (III), $R_7$ is additionally 3-($C_1-C_4$alkoxy)propyl, or $R_6$ and $R_7$, together with the nitrogen atom to which they are linked, form 5,5,7-trimethyl-1,4-diazepan-1-yl, $R_9$ is $C_2-C_6$alkylene and $R_{10}$ and $R_{11}$ are independently of one another $C_1-C_4$alkyl.

13. A compound of the formula (I) according to claim 1, characterized in that said compound is 2-[N,N-bis(2,2,6,6-tetramethyl-4-piperidyl)amino]-4,6-bis[tetrahydrofurfurylamino]-1,3,5-triazine,
2-[N,N-bis(2,2,6,6-tetramethyl-4-piperidyl)amino]-4,6-bis[5,5,7-trimethyl-1,4-diazepan-1-yl]-1,3,5-triazine,
2-[N,N-bis(2,2,6,6-tetramethyl-4-piperidyl)amino]-4,6-bis[N-(2,2,6,6-tetramethyl-4-piperidyl)-tetrahydrofurfurylamino]-1,3,5-triazine,
2-[N,N-bis(2,2,6,6-tetramethyl-4-piperidyl)amino]-4,6-bis[1,2,2,6,6-pentamethyl-4-piperidyloxy]-1,3,5-triazine, 2,4-bis[N,N-bis(2,2,6,6-tetramethyl-4-piperidyl)amino]-6-[3-(diethylamino)propylamino]-1,3,5-triazine, 2-[N,N-bis(1,2,2,6,6-pentamethyl-4-piperidyl)amino]-4,6-bis[1,2,2,6,6-pentamethyl-4-piperidyloxy]-1,3,5-triazine, 2,4-bis[N,N-bis(1,2,2,6,6-pentamethyl-4-piperidyl)amino]-6-[3-(diethylamino)propylamino]-1,3,5-triazine, 2-[N,N-bis(2,2,6,6-tetramethyl-4-piperidyl)amino]-4,6-bis[n-dodecylthio]-1,3,5-triazine, 2,4-bis[N,N-bis(2,2,6,6-tetramethyl-4-piperidyl)amino]-6-[n-dodecylthio]-1,3,5-triazine, or 2-[N,N-bis(2,2,6,6-tetramethyl-4-piperidyl)amino]-4,6-bis[N-(2,2,6,6-tetramethyl-4-piperidyl)-3-methoxypropylamino]-1,3,5-triazine.

14. A compound of the formula (I) according to claim 1, characterized in that said compound is 2-[N,N-bis(2,2,6,6-tetramethyl-4-piperidyl)amino]-4,6-bis[N-(2,2,6,6-tetramethyl-4-piperidyl)-tetrahydrofurfurylamino]-1,3,5-triazine, 2-[N,N-bis(2,2,6,6-tetramethyl-4-piperidyl)amino]-4,6-bis[1,2,2,6,6-pentamethyl-4-piperidyloxy]-1,3,5-triazine, 2,4-bis[N,N-bis(2,2,6,6-tetramethyl-4-piperidyl)amino]-6-[3-(diethylamino)propylamino]-1,3,5-triazine, 2-[N,N-bis(1,2,2,6,6-pentamethyl-4-piperidyl)amino]-4,6-bis-[1,2,2,6,6-pentamethyl-4-piperidyloxy]-1,3,5-triazine, 2,4-bis[N,N-bis(2,2,6,6-tetramethyl-4-piperidyl)amino]-6-[n-dodecylthio]-1,3,5-triazine, or 2-[N,N-bis(2,2,6,6-tetramethyl-4-piperidyl)amino]-4,6-bis[N-(2,2,6,6-tetramethyl-4-piperidyl)-3-methoxypropylamino]-1,3,5-triazine.

15. A compound of the formula I(a)

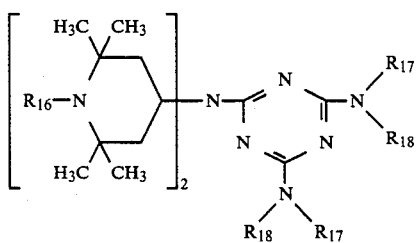

wherein $R_{16}$ is benzyl, the radicals $R_{17}$ are independently of one another $C_1$-$C_{18}$alkyl and the radicals $R_{18}$ are independently of one another hydrogen or a group of the formula (IV)

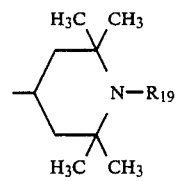

where $R_{19}$ is benzyl.

16. A compound of the formula (Ia) according to claim 15, wherein $R_{16}$ is hydrogen or methyl, the radicals $R_{17}$ are identical and are $C_1$-$C_8$alkyl and the radicals $R_{18}$ are identical and are 1,2,2,6,6-pentamethyl-4-piperidyl or 2,2,6,6-tetramethyl-4-piperidyl.

17. A compound of the formula (Ia) according to claim 15, characterized in that said compound is 2-[N,N-bis(1,2,2,6,6-pentamethyl-4-piperidyl)amino]-4,6-bis[N-(1,2,2,6,6-pentamethyl-4-piperidyl)-n-butylamino]-1,3,5-triazine.

18. A compound of the formula (Ib)

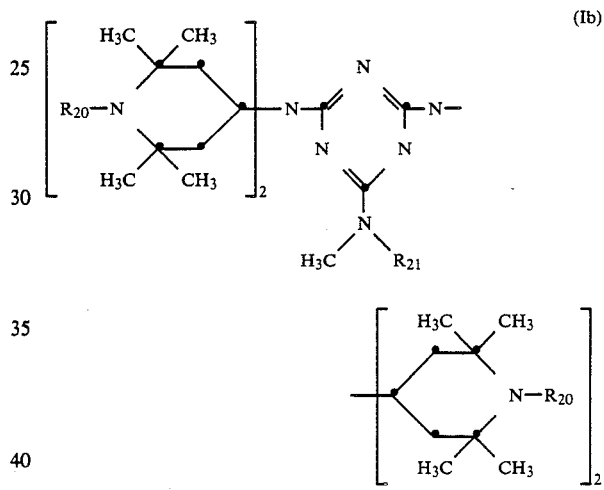

wherein the radicals $R_{20}$ are independently of one another hydrogen or methyl and $R_{21}$ is $C_8$-$C_{18}$alkyl.

19. A compound of the formula (Ib) according to claim 18, wherein the radicals $R_{20}$ are benzyl.

20. A compound of the formula (Ib) according to claim 18, characterized in that said compound is 2,4-bis[N,N-bis(1,2,2,6,6-pentamethyl-4-piperidyl)amino]-6-[N-(methyl)-n-octylamino]-1,3,5-triazine or 2,4-bis[N,N-bis(1,2,2,6,6-pentamethyl-4-piperidyl)amino]-6-[N-(methyl)-n-dodecylamino]-1,3,5-triazine.

* * * * *